United States Patent
Seitz et al.

(10) Patent No.: US 8,921,093 B2
(45) Date of Patent: Dec. 30, 2014

(54) ARRANGEMENT FOR ON-LINE MEASUREMENTS ON CELLS

(75) Inventors: Daniel Seitz, Bindlach (DE); Helmar Mayr, Kaufering (DE); Guenter Ziegler, Bayreuth (DE); Winfried Vonau, Geringswalde (DE); Frank Gerlach, Waldheim (DE); Sigrun Herrmann, Waldheim (DE)

(73) Assignee: BioCer Entwicklungs GmbH, Bayreuth (DE)

( * ) Notice: Subject to any disclaimer, the term of this patent is extended or adjusted under 35 U.S.C. 154(b) by 1095 days.

(21) Appl. No.: 12/309,572

(22) PCT Filed: Jul. 23, 2007

(86) PCT No.: PCT/DE2007/001326
§ 371 (c)(1),
(2), (4) Date: Sep. 22, 2009

(87) PCT Pub. No.: WO2008/011876
PCT Pub. Date: Jan. 31, 2008

(65) Prior Publication Data
US 2010/0015656 A1    Jan. 21, 2010

(30) Foreign Application Priority Data
Jul. 24, 2006 (DE) .......................... 10 2006 034 606

(51) Int. Cl.
| | | |
|---|---|---|
| C12Q 1/02 | (2006.01) | |
| G01N 27/26 | (2006.01) | |
| C12M 1/34 | (2006.01) | |
| G01N 33/543 | (2006.01) | |
| B01L 3/00 | (2006.01) | |

(52) U.S. Cl.
CPC ...... *G01N 33/5438* (2013.01); *B01L 3/502707* (2013.01); *C12M 41/32* (2013.01); *C12M 41/34* (2013.01); *B01L 2200/02* (2013.01); *B01L 2300/0627* (2013.01); *B01L 2300/0645* (2013.01); *B01L 2300/163* (2013.01)
USPC .... 435/287.1; 435/29; 435/286.2; 435/303.1; 435/383; 204/403.1

(58) Field of Classification Search
CPC .......... B01L 3/502707; B01L 2200/02; B01L 2300/0627; B01L 2300/163; B01L 2300/0645; G01N 33/5438; C12M 41/32; C12M 41/34; C12M 23/22; C12M 23/24; C12M 41/46; C12M 23/54; C12M 23/42
USPC ............... 435/287.1, 29, 293.1, 286.2, 303.1, 435/383; 204/403.9
See application file for complete search history.

(56) References Cited

U.S. PATENT DOCUMENTS 4,748,124 A * 5/1988 Vogler .......................... 435/401
5,614,378 A    3/1997 Yang et al.
(Continued)

FOREIGN PATENT DOCUMENTS

DE    4115792    11/1992
DE    4417079    12/1995
(Continued)

OTHER PUBLICATIONS

Jul. 29, 1994 Spectrophotometric flow-through gas sensor for the determination of atmospheric ntrogen dioxide D. Schepers et al. Analytica Chimica Acta vol. 308 pp. 109-114.

*Primary Examiner* — William H Beisner
*Assistant Examiner* — Danielle Henkel
(74) *Attorney, Agent, or Firm* — Jordan and Hamburg LLP

(57) ABSTRACT

The invention relates to an arrangement (a measurement device) for on-line measurements on cells, in particular for measuring soluble analytes and dissolved gases on samples in a sample area.
The object of the invention, to specify an arrangement for on-line measurements in order to investigate and monitor the metabolism of living cells, which avoids the disadvantages of the prior art and can be integrated in a microfluidic system in the process, is achieved in that the arrangement comprises a substrate, at least one sensor, a sample analysis space and a membrane with the substrate holding the sensor or the sensors and the membrane in such a way that the sample analysis space is generated between the sensor or sensors and the membrane, with the membrane having the capability to be connected in a biocompatible form and to a cell culture space with the sensor or sensors being electrochemical sensors, and in which the sample analysis space can be filled with a transfer medium and can be integrated in fluidic systems, and the sensor sensors is or are fitted with operating circuits via which downstream electronics can be coupled.

13 Claims, 1 Drawing Sheet

(56) References Cited

U.S. PATENT DOCUMENTS

| | | | |
|---|---|---|---|
| 6,455,310 B1 * | 9/2002 | Barbera-Guillem | 435/383 |
| 2005/0089993 A1 * | 4/2005 | Boccazzi et al. | 435/286.2 |
| 2006/0275896 A1 * | 12/2006 | Anderson et al. | 435/303.1 |

FOREIGN PATENT DOCUMENTS

| | | |
|---|---|---|
| DE | 19646505 | 5/1998 |
| DE | 19753598 | 7/1999 |
| DE | 19903506 | 8/2000 |
| DE | 19860547 | 10/2000 |
| DE | 19924856 | 12/2000 |
| DE | 100 03 673 | 8/2001 |
| DE | 69729185 | 11/2004 |
| EP | 0289269 | 11/1988 |
| WO | WO-87/05624 | 9/1987 |
| WO | WO-96/32467 | 10/1996 |
| WO | WO-03/036293 | 5/2003 |
| WO | WO-03/082469 | 10/2003 |
| WO | WO-2005/097969 | 10/2005 |
| WO | WO-2006/037022 | 4/2006 |

\* cited by examiner

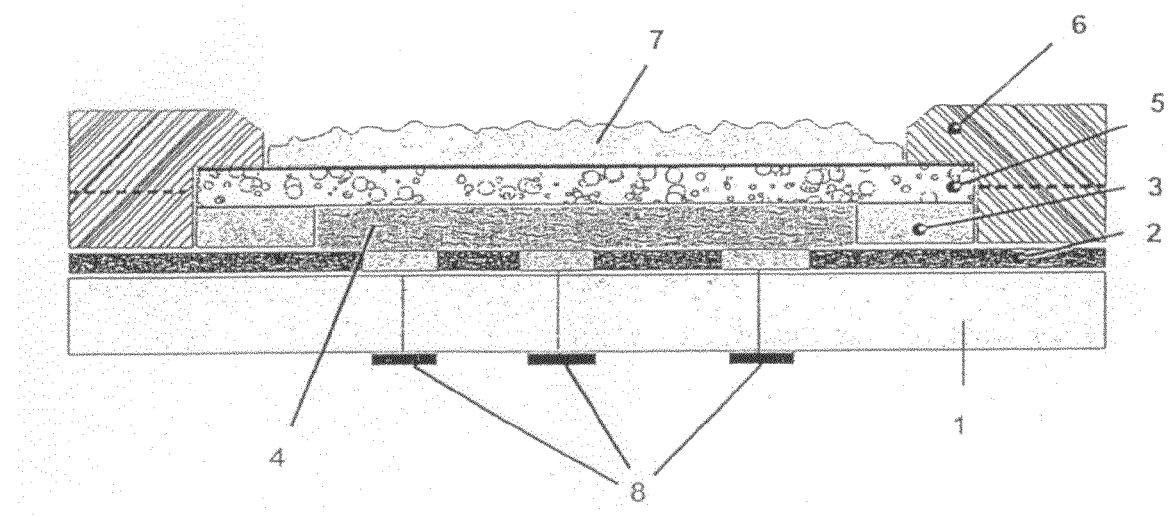

ARRANGEMENT FOR ON-LINE MEASUREMENTS ON CELLS

BACKGROUND OF THE INVENTION

The invention relates to an arrangement (a measurement device) for on-line measurements on cells, in particular for measuring soluble analytes and dissolved gases on samples in a sample area.

The behavior of cell cultures, particularly with regard to the metabolic-physiological parameters, can be detected by using very different electro- or biochemical sensors.

DE 41 15 792 describes for example a principal arrangement for a biosensor system that is suitable for biochemical measuring methods by using a membrane-covered miniature electrode and is equipped with a membrane-clamping and membrane-replacing unit.

According to this publication, the counter electrode of the miniature electrode is shaped like a spherical cap that is provided with a center aperture in which the head of the meter electrode is arranged.

The membrane-clamping and membrane-replacing unit consists of a hinged lower part for changing the membrane and a second lower part, which is connected to the first lower part, can be let down and in the first mentioned lower part the membrane is pre-clamped and sealed by a Teflon ring in a cylindrical recess that is expanding a through hole.

The membrane is clamped again by the head of the miniature electrode via the center hole in the Teflon ring and sealed again by the upper edge of the isolation body.

However, this basic arrangement cannot be used for on-line measurements on cell cultures over longer periods of time because principally the membrane cannot be integrated in the sample area and is not designed for the culture of cells. Particularly, adherent cell cultures require a stable, immobile substrate. In the described arrangement, an interference-free separation of the culture space and the sensors is not possible.

In fact, it cannot be avoided that the electrochemical sensors used for the detection of the behavior of cell cultures can only record correct measured values over a limited period.

It is a generally known fact that almost all chemosensors and all biosensors, for which chemosensors mostly form the basic sensor, require a constant recalibration because for functional reasons relatively thin layers or layer systems of different compositions, organic and/or inorganic crystalline or amorphous membranes or possibly fluid functional elements are, among others, components of the sensor. Depending on several parameters (age, environment, pressure, temperature, etc.) they are subject to a change in the material that directly affects the generated sensor signal.

Thus, the arrays occupied by the cells of a cell culture can normally be used in experiments for a maximum period of only three days. That is that the usability for the online measurement is restricted to processes that can be performed within this period completely or at least to such a point at which a significant statement can be made about the course of the metabolism in question.

A lot of the suited sensor materials are not only disturbed by a coating of cells and proteins, but also their biocompatibility can be impaired. Thus, particularly adherent cells that show a sensitive reaction to the nature of the substrate cannot be analyzed in their natural condition.

For the cultivation of cells in general and for the three-dimensional, multi-layer tissue engineering implants in particular (e.g. non-vascular artificial cartilages) the control of the nutrients absorbed by the metabolism of the cells is essential for the successful cultivation during longer periods. For this it is advantageous to measure at least the physiologically important parameters oxygen, glucose and pH-value in the lowest cell layers.

So far, the determination of these parameters has been accompanied by the destruction of the samples or said parameters have been tested indirectly by measuring the culture medium. Fluorescence-based systems with fluorophores embedded in silicone are recently available but adherent cells do not grow on them. The use of the above described sensor-array systems has to be ruled out because of the impossibility of recalibration during the cultivation process.

Therefore, one of the most serious problems in the use of electrochemical sensors is the interaction of the sensor surface with the sample. Substances, such as organic molecules or proteins, can interact with the sensor and thus reduce the sensitivity of the sensor. Moreover, problems can arise when measuring live systems that can be negatively influenced by the sensor surface, e.g. by silver/silver chloride reference electrodes.

According to the prior art, fluorescence-based systems are known that are mostly bioinert and thus principally suited for the measurement on suspension cell cultures but only few adherent cell types, if at all, can grow on these systems. Such a system is, for example, disclosed in DE 199 03 506, DE 100 03 673 and WO 03/036293.

A further disadvantage of such fluorescence-based systems is the low number of fluorophore systems that are available at present.

Sensor systems that allow the direct growth of adherent cells are, for example, mentioned in DE 197 53 598, DE 196 46 505, DE 44 17 079 and DE 196 46 505.

In these systems, a compatibility with the cell growth is achieved by operating with silicone-based sensors that are manufactured in thin-film technology. This technology, which has its own fields of application, e.g. the measurement on individual cells, causes some problems in the routine application in cell and tissue cultures. In particular, the silicone used is only a very special material for the adhesion of the cells. The silicone wafer that is moreover provided with further metallic materials in CMOS technology is a very special substrate for the adhesion of cells. As in the cell development it is precisely the interaction of the tissue cells with the substrate that plays a decisive role, a neutral substrate that is, above all, not influenced by electric currents (for amperometric sensors) and by diverse metal ions would be of utmost importance for the examination of more than just some specific questions.

If the behavior of cell cultures is detected on-line by means of electrochemical sensors, it cannot be avoided that a recalibration should be performed if the cells grow directly on the sensors. But this is not possible at present. Furthermore, it is just the manipulation at the cell or tissue culture that should be avoided during the on-line measurement. Normally, the arrays occupied by the cells can be used for maximally three days only. That is that the usability for the online measurement is limited to processes that are completely finished within this period or reach a point at which a significant statement about the course of the metabolism in question can be made.

Another problem will arise, if integrative total values are to be measured instead of punctual, local values of individual cells. Each of the sensors arranged one next to the other measures under another cell group and the given variability of biological systems complicates the correlation of the parameters measured in this way.

Finally, the production of sensors in thin-film technology implies efforts and expenses and therefore it is only economically practical for a larger volume.

However, the thick-film technology that offers higher flexibility and is much less expensive than the thin-film technology leads to the same disadvantages for the provided sensors as the thin-film technology.

Another problem is caused by the sterilization required for all parts that come into contact with the sample area. Here, a difference must be made between the simple disinfection that can be sufficient for short measuring phases and the sterilization that can be harmful for example for enzymes in biosensors. The most common sterilization method applied in laboratories is the high-pressure sterilization (in the autoclave).

Membranes are often used in combination with sensors. However, the membranes have been directly connected with the sensor so far. (For this, see WO 87/05624, DE 697 29 185 T1 and DE 199 24 856 A1, among others, where the functional selectivity is in the focus of attention for these sensors or the membrane referred to is an enzyme-carrying layer.)

The most important disadvantage of this technical solution is the fact that a multi-parametric analysis of the same sample and the recalibration required for the on-line measurement over longer periods are not possible.

In DE 694 11 732 T1 and EP 0289269, the specific function of the membrane is the exclusion of erythrocytes in blood analyses.

In WO 199 6032 64 A1, the cells are actually cultivated on a membrane, but the physiological parameters are measured by a sensor that is positioned in the cultivated tissue and thus influences the cultivation or changes the conditions.

The paper of D. Schepers, G. Schulze and W. Frenzel ["Spectrophotometric flow-through gas sensor for the determination of atmospheric nitrogen dioxide" (Analytika Chimica Acta 308 (1995) 109-114] describes a micro measuring cell for fluids that is particularly used for photometers or spectrometers, which preferably operate in a narrow band application, and contains two-dimensionally connected wafers that are provided with micro-channels in such a way that at least in one area two micro-channel sections are arranged parallel to each other and spatially separated from each other by a selective membrane chosen according to a substance to be analyzed so that an extraction path is formed, and the first wafer is provided with at least the first micro-channel section mentioned and its inlet and outlet openings or inlet and outlet channels combined with the ends of said channel section to transfer an analyte, and a second wafer is provided with at least the second micro-channel section mentioned and the inlet and outlet openings or inlet and outlet channel combined with the ends of said channel section to transfer an extraction means (E), and at least one wafer is transparent for a measurement light ray used for the measuring process or it is provided with a window range ensuring this, and the inlet and outlet of the measuring light ray is defined by the second micro-channel section used as an extraction channel so that, depending on the light source (L) used, an optical measuring path as long as possible is achieved.

The just mentioned micro measuring cell for fluids does not allow an on-line measurement of different physiological parameters of cells of one cell culture, in particular the measurement of soluble analytes and dissolved gases because specific sensors are not provided for the on-line measurement of soluble analytes and dissolved gases.

DE 198 60 547 A1 describes an affinity sensor for the detection of specific bond types consisting of a carrier substrate that is at least provided with two electrodes that are arranged at an equidistant distance one to the other and cover an area on both sides and at least said area is provided for the uptake of immobilized specific bonding partners that are capable to couple complementarily associated bonding partners directly or via further specific bonding molecules and said area is defined with a minimum width such that at least one complementarily associated bonding partner provided with an electrically conductive particle can be taken up in the mentioned area in such a manner that the possibility of the formation of a tunnel contact transfer is ensured between the particle and each electrode.

The just mentioned affinity sensor does not allow an on-line measurement on cells, in particular the measurement of soluble analytes and dissolved gases, because only specific couplings of bonding molecules can be electrically detected.

SUMMARY OF THE INVENTION

Therefore, it is the object of the present invention to specify an arrangement for on-line measurements in order to investigate and monitor the metabolism of living cells and said arrangement avoids the described disadvantages of the prior art and can be integrated in a microfluidic system.

It must be ensured for the arrangement to be provided that the multisensor system can be often recalibrated without disturbing the cultivation process so that first long-term studies about the metabolism of the biological material are possible in dependence on the selected cultivation conditions and secondly soft and hard tissues can also be cultivated under controlled conditions and such a process normally requires periods of >96 hours.

Moreover, the surface of the arrangement to be described shall be biocompatible to the cell culture and allow an adherent growth.

Further, it is to be ensured that the cell growth (particularly for adherent cells) is not impaired by any kind of manipulation possibly combined with the calibration of the sensor array.

Finally, it must be possible to sterilize all parts of said arrangement that come into contact with the cells or their culture medium, advantageously by high-pressure steam sterilization (treated by autoclave).

The invention is based on an arrangement that can be principally used for any types of sensors to perform measurements on liquid samples or samples contained in liquids, regardless of whether said samples have an influence on the medium or can be affected by the medium, and in this procedure the species to be measured diffuse through the membrane in a defined manner and come to a space/area that is filled with a defined test liquid and located directly above the sensor.

In this technical solution, the cell culture space can be uncoupled and is separated from the sensor field by a membrane.

The present invention comprises a sensor system in which different types of sensors, planar sensors in a special embodiment, are miniaturized and arranged one next to the other in the smallest possible space. The sensors are to be designed in such a way that they do not influence each other. The primary downstream electronic unit being in direct contact with the sensors must be provided such that the galvanic separation of the contacts is ensured.

This sensor array can be produced, for example, in screen printing technology.

Moreover, the invention contains a membrane that allows an optimum analyte transport but inhibits a convection of the media through the membrane as far as possible. The pores must be designed so that during an optimum diffusion of the analytes to be measured such substances are held back that could be impair or disturb the sensors, for example proteins, fine particles etc.

Advantageously, the membrane is biocompatible or bioinert to allow a non-destructive measurement on cells or tissues. The latter can be included in suspension or grow adherently on the membrane. Possible membrane materials are polymers, polymer blends and co-polymers, ceramics, metals and alloys, glass and composites.

The membrane of hydroxylapatite is particularly advantageous so that bones/cartilage cultures can be cultivated adherently on the material. If cells are cultivated, the inventive arrangement will show the particular advantage that physiological parameters of cell/tissue cultures can be measured continuously over a period of several weeks. Moreover, the arrangement allows to register important biological parameters below the adherent cell/tissue culture, to say of the cell layers that are provided with the fewest nutrients.

The nano-porous structure of the membrane causes the separation of the two systems (culture medium and transfer medium) and maintains the sterility of the cell/tissue culture.

A method for producing these membranes is based on the use of classified ceramic powders so that a very narrow pore radius distribution is achieved in the production of the membrane and this has a positive effect on the membrane function (e.g. selectivity regarding the analyte transport).

The present invention includes a coupling system that separates the measurement device from the sample area. This design allows
  recalibration by decoupling and coupling calibration solutions,
  the replacement of sensors for extending the parameters that can be measured,
  the replacement of sample areas for serial measurements of several samples, e.g. in an automatic device that allows the serial measurement of several membrane/sample area units.

The coupling system can be designed for example as a bayonet lock, as a screw-type lock or as a system tightened by screws (that can be moved by a motor or a motor gear box) and provided with sealing rings.

In this invention, the space (gap) that can be filled with a transfer medium can be coupled with fluidic systems so that the transfer medium (defined test liquid) can be pumped into the space (gap) between the sensor field and the bottom surface of the membrane or can be let out and replaced. Moreover, calibration solutions can be used for the automatic calibration.

The inventive solution is based on the separation of the cell culture space and the sensor field by a biocompatible porous membrane. In this way, the sensory system can be effectively miniaturized and optimized, the cells grow on a suited substrate and the measurement is ensured at the lower, mostly nutritive-limited cell layers.

An arrangement is represented in which the bottom of a well for the cell culture is formed by a biocompatible porous membrane and a sensor array with downstream electronics can be coupled to the lower surface of said well bottom. Said sensor array has been produced in planar technologies and functions on an electrochemical principle.

To be used in the cell culture, the sensor field is provided on the area of one well of possibly several well shells. For this purpose, the sensory, electronic and fluidic structures require considerable miniaturization. The sensors record the relevant measurement parameters simultaneously and thanks to the complete galvanic separation they do not influence each other.

The membrane set in an appropriate plastic material is the cell culture system and is connected with the sensor unit via a coupling system so that a recalibration is possible by decoupling.

The arrangement with the sample area consists, for example, of polymers, polymer blends and co-polymers, ceramics, metals and alloys, glass and composites.

The membrane of this arrangement is designed as a porous membrane that consists, for example, of polymers, polymer blends, co-polymers, metals and alloys, glass and/or composites.

In an advantageous embodiment, the membrane is made of ceramics in homogeneous structure or a structure consisting of layers. It can be either biocompatible or bioinert.

In a particularly advantageous embodiment of this invention, the membrane is made of hydroxylapatite or laminated ceramics with a surface of hydroxylapatite that forms an osteo-inductive substrate for the cell culture.

The membrane can be modified for functional reasons in such a way that a cell adhesion, the cell growth or other cell behavior can be influenced.

The size of the pores is advantageously smaller than 0.3 $\mu$m so that a sterile separation of the sample area and the outside is ensured.

A particularly advantageous embodiment includes a membrane that has a very narrow monomodal pore radius distribution so that a clear separation border and a timely narrow-distributed diffusion behavior of the analytes are guaranteed.

The present invention allows to perform a procedure for measuring cell and tissue cultures in which the samples to be measured are included in a space that is isolated from the measurement device by a porous membrane so that the analytes to be measured diffuse through the membrane, the samples do not interact with the materials of the measurement device and the measurement device is protected from damage or disturbing influences of the samples.

In this procedure, the arrangement can comprise one sensor or several sensors with downstream electronics and the sample area and the membrane can be separated from the measurement device so that a recalibration or a replacement of the measurement device is possible.

The membrane isolates the sample area in such a way that it forms a sterile and closed system after being separated from the measurement device.

The inventive use of the biocompatible membrane allows to provide suited surfaces for the cells that will even be an ideal substrate for bone-cartilage cultures if hydroxylapatite is used.

The arrangement is designed as a cell culture vessel for the cell and tissue-culture. Here, the membrane is the bottom of the vessel so that this procedure allows, among others, measurements at the lower layers that are least supplied by the medium.

The advantageous feature of the inventive arrangement is the fact that the sample area and the membrane can be sterilized separately or together (e.g. by autoclave).

The coupling system of the inventive arrangement allows the separation of the measurement device from the sample area with the membrane so that several coupling and uncoupling actions are possible and a defined gap distance can be generated between the sensors and the bottom side of the membrane.

Moreover, according to this invention the arrangement is designed as a sensor head that can be coupled consecutively to the membranes of a sample unit with several individual sample-area-membrane-units so that samples can be probed one after the other automatically.

In the following, the exemplary embodiments explain the invention in detail.

BRIEF DESCRIPTION OF THE DRAWING

FIG. 1 shows the basic functional principle of the present invention.

DETAILED DESCRIPTION OF THE INVENTION

On a substrate 1, planar electrochemical sensors 2 are provided that are miniaturized in thick film and dispenser technologies so that always one oxygen sensor, one pH sensor and one glucose sensor are positioned on an area of ca. 1.75 $cm^2$ and connected to sensor-close operating circuits 8.

The cell culture space 7, in which the cell cultivation is performed, is separated from the planar sensors 2, which have been produced in thick-film technology, by a defined permeable biocompatible membrane 5 having a thickness of between 0.5 and 2 mm, being made of hydroxylapatite and being provided with an absolutely planar bottom surface and the mean pore size distribution is between 100 and 200 nm and the porosity is between 20 and 60%. The maximum pore diameter is 300 nm and thus a sterile barrier is generated towards the cell culture space 7 (sample area). Moreover, a suitable transfer medium offers the possibility of interaction between the species to be measured and the sensors 2.

The entire cell culture space can be taken off the substrate plate 1 (sensor plate) and sealed laterally against liquids so that a common space 4 (gap) is formed that can be filled with a transfer medium by means of microfluidic systems. The space 4 is sealed towards the membrane with sealing rings.

Defined peripheral conditions are given by a spacer 3 arranged between the substrate plate 1 (sensor plate, e.g. in form of a sensor array) and the membrane 5. It does not only ensure the mechanical stability of the membrane 5 but also a uniformly thick electrolyte film.

Thanks to an appropriate closing element provided at the edge the inventive system that is equipped with a coupling/decoupling option, which constitutes a coupling mechanism 6, can be recalibrated and thus the period of cultivation is not limited any longer in this point.

Contrary to the prior art, the inventive solution allows to cultivate cells on an optimum substrate and nevertheless important substance concentrations can be measured by means of precise sensor electronic without any interference. In three-dimensional constructs it is possible to perform non-invasive and reliable measurements in the lower layers. The coupling mechanism provides a calibration option for the sensor system. Moreover, the sensor signals are not falsified by sensors partly covered with biological cells and the resulting diffusion inhibition. In addition to this, an optimum, biocompatible substrate can be even provided for the cells for an adherent growth. Here, even a functionalizing biological coverage can be applied.

The inventive arrangement according to FIG. 1 can comprise numerous sensors arranged to one array (for example different sensors the specific analytes of which can be registered simultaneously). And the planar miniaturized sensors that are arranged one next to the other are designed in such a way that they do not influence one another. The design of the primary transfer electronics being in direct contact with the sensors ensures the galvanic separation of the contacts. Several measuring cells of such type can be arranged next to the other so that several samples can be measured simultaneously but independently from each other.

The membrane(s) 5 can be adjusted to the requirements of the cell culture by surface modification. Said modification can be a structuring, a chemical modification for setting the hydrophilic/hydrophobic property, a coupling of bioactive molecules or another surface modification. The is only important fact is that the measurement is not disturbed by the membrane(s) 5.

In the example, the coupling mechanism 6 (coupling system) is realized by a laterally sealed space that allows the lifting and lowering of the cell culture space 7 with the membrane 5 relative to the sensors 2. In this way, the space 4 (gap) can be extended and rinsed as a whole with liquid. After lowering, sealing rings under the membrane 5, which are not shown in FIG. 1, enclose an isolated gap with the sensors 3 so that the measurement can be started. An advantage of this embodiment is the possibility to operate especially well without any air bubbles.

In another embodiment of this invention, the inventive arrangement is integrated in vessels in such a manner that a continuous measurement on the vessel contents is possible. In a special version the vessels are cell or tissue culture dishes. Here, the instrument can be installed in the medium area, e.g. in the wall of bioreactors for the suspension culture, or directly under the adherently growing cells. This unit can be integrated as a kit in different fields of applications.

Another embodiment includes an arrangement in form of such a multi-well plate that is for example used for the cell culture. Here, the membrane 5 forms the bottom of each well and under each well a sensor array with microfluidics is provided so that a simultaneous measurement under each well is possible. In this arrangement, the substrate is connected such that it is either fixed or that it can be replaced so that several plates can be measured one after the other by coupling and decoupling. In one version, this plate is integrated into a device with the complete measurement unit, including the control unit for temperature, gas composition and air humidity, so that the samples can be incubated during continuous measurements. In another embodiment, the instrument is compact and its construction allows the integration of the total measurement device in one cell culture incubator.

In a further inventive embodiment, the arrangement includes a measuring head with a sensor array and microfluidics that—by coupling and decoupling—repeatedly moves by means of a robotic system to several measuring points in a measurement plate comprising several sample areas, which are limited by the membrane and the coupling system at the bottom, and thus performs the measurements one after the other. The advantage of this embodiment is the fact that more space is provided for the downstream electronics and the microfluidics although the sensor area or the measurement gap has the same size.

Another inventive embodiment integrates the arrangement into a bioreactor, either for controlling suspension cultures or cultures in reactors adapted to the tissue culture, e.g. flow or pressure perfusion reactors.

The inventive arrangement allows to perform investigations in cell physiology that have not been possible by means of the arrangements and investigation methods used so far.

Thus, measurements can be simultaneously performed by using one sensor or several sensors arranged in a sensor array even for such samples for which it is important to avoid their direct contact to the sensor. Here, it is advantageous, if the sample area and the sensor unit can be separated from each other by a coupling system in order to allow i) the replacement of the sensor system or the sample area,
ii) recalibration and
iii) the cleaning of the measurement device.

The inventive arrangement allows the effective measurement of cell and tissue cultures over a longer period of time, e.g. in an array of different analytes (such as pH, glucose, oxygen).

In this way it is for example possible to adjust the sensor system of the described arrangement under a standard cell culture unit (15 mm Ø well of a culture dish) to be able to analyze several parameters and to do this in an economic manner.

The advantage of the inventive arrangement is that tissue cultures can be measured during longer periods, and the sample area surface is sterile and biocompatible and the values can also be measured under a tissue or cell layer because the measurement of the parameters to be determined is possible from the bottom due to the supporting surface of the inventive design so that the problems of cell physiology that could not be investigated so far can be tackled now.

In the special case of bone- and/or cartilage cells the inventive arrangement has the advantage that the membrane of hydroxylapatite is compatible with these cells and can be combined with them.

All elements presented in the description, the subsequent embodiment example and the drawing can be decisive for the invention both as single elements and in any combination.

The invention claimed is:

1. Apparatus for online measurement of samples from a cell culture space, the samples containing soluble analytes and dissolved gases, the apparatus comprising
   a substrate,
   at least one sensor provided with at least one operating circuit,
   a membrane, the substrate supporting the at least one sensor and the membrane so as to form a sample analysis space between the at least one sensor and the membrane, the membrane being removably attachable with respect to the at least one sensor by a coupling mechanism so as to enable detachment of the membrane and the cell culture space defined thereby with respect to the at least one sensor in order to expose the sample analysis space formed between the at least one sensor and the membrane, and
   a spacer interposed between the coupling mechanism and the at least one sensor so that the spacer is positioned directly beneath the membrane and adjacent the at least one sensor and beyond a terminal portion of the coupling mechanism, said terminal portion of the coupling mechanism extending toward a center of the apparatus when said apparatus is viewed in cross-section so that said spacer is positioned proximal the center of the apparatus and nearer thereto than said terminal portion of the coupling mechanism, a portion of the spacer distal the center of the apparatus being abutted with the coupling mechanism when the coupling mechanism couples the membrane with respect to the at least one sensor,
   the membrane being biocompatible or bioinert and communicable with the cell culture space, the sample analysis space being fillable with a transfer medium and integratable with a fluidic system, and the at least one operating circuit being couplable to downstream electronics.

2. Apparatus according to claim 1, wherein the at least one sensor is an electrochemical sensor.

3. Apparatus according to claim 1, wherein the membrane is porous and comprises a ceramic, polymer, polymer blend, copolymer, metal, alloy, glass and/or composite.

4. Apparatus according to claim 1, wherein the membrane is porous, pores of the membrane being smaller than 0.3 mm.

5. Apparatus according to claim 1, wherein the membrane is porous and has a very narrow, monomodal pore radius distribution.

6. Apparatus according to claim 1, wherein thickness of the membrane is from 0.5 to 2 mm.

7. Apparatus according to claim 1, wherein the membrane comprises a multilayer ceramic array having an upper layer suitable for contact with cells of a cell culture, the upper layer comprising hydroxylapatite and all the layers having like size, proportion and distribution of pores.

8. Apparatus according to claim 1, wherein the membrane is porous and comprises hydroxylapatite and the membrane has a mean pore size distribution of 100 to 200 nm, maximum pore diameter or 300 nm and porosity of 20 to 60%.

9. Apparatus according to claim 1, wherein the sensors do not have a physico-chemical influence on each other.

10. Apparatus according to claim 1, wherein the at least one sensor is planar.

11. Apparatus according to claim 1, wherein the sensors comprise an oxygen sensor, a pH sensor and a glucose sensor supported by the substrate on an area of about 1.75 $cm^2$.

12. Apparatus according to claim 1, wherein the cell culture space and the membrane are sterilizable or treatable by autoclave separately or together.

13. A method of obtaining online measurement of samples from a cell culture space, the samples containing soluble analytes and dissolved gases, the method being performed with the apparatus of any one of claims 1 to 12 and comprising
   introducing a cell culture into the cell culture space,
   permitting analytes to diffuse through the membrane mid enter the sample analysis space, by means of the at least one sensor measuring at least one physical or chemical parameter of the sample in the sample analysis space for recordation and analysis by the downstream electronics, and,
   at time intervals, separating the cell culture space and the membrane from the apparatus so as to enable recalibrating or replacing of the substrate, at least one of the sensors, the sample analysis space and/or the membrane.

* * * * *